United States Patent
Lv et al.

(10) Patent No.: US 11,904,304 B2
(45) Date of Patent: Feb. 20, 2024

(54) ZEOLITE-LIKE MATERIAL, AND PREPARATION METHOD AND USE THEREOF

(71) Applicants: Tibet University, Lhasa (CN); Tianjin Chengjian University, Tianjin (CN)

(72) Inventors: Xuebin Lv, Lhasa (CN); Wenli Feng, Lhasa (CN); Jian Xiong, Lhasa (CN); Guanyi Chen, Lhasa (CN); Rui Zhang, Lhasa (CN); Shijie Yang, Lhasa (CN); Jianguo Cui, Lhasa (CN); Wei Li, Lhasa (CN); Zeng Dan, Lhasa (CN); Duo Bu, Lhasa (CN)

(73) Assignees: Tibet University (CN); Tianjin Chengjian University (CN)

( * ) Notice: Subject to any disclaimer, the term of this patent is extended or adjusted under 35 U.S.C. 154(b) by 0 days.

(21) Appl. No.: 17/727,225

(22) Filed: Apr. 22, 2022

(65) Prior Publication Data

US 2023/0271171 A1 Aug. 31, 2023

(30) Foreign Application Priority Data

Feb. 28, 2022 (CN) .......................... 202210185397.0

(51) Int. Cl.
| | | |
|---|---|---|
| C01B 39/02 | (2006.01) | |
| B01J 29/76 | (2006.01) | |
| B01J 37/00 | (2006.01) | |
| B01J 37/04 | (2006.01) | |
| B01J 37/08 | (2006.01) | |
| C07D 307/33 | (2006.01) | |

(52) U.S. Cl.
CPC ............ B01J 29/76 (2013.01); B01J 37/0063 (2013.01); B01J 37/04 (2013.01); B01J 37/082 (2013.01); C01B 39/02 (2013.01); C07D 307/33 (2013.01); B01J 2229/42 (2013.01); C01P 2002/82 (2013.01); C01P 2004/03 (2013.01)

(58) Field of Classification Search
CPC .... C01P 2002/82; C01P 2004/03; C01B 9/02; C07D 307/33; B01J 29/04; B01J 29/061; B01J 29/072; B01J 29/76; B01J 29/70; B01J 2229/24; B01J 2229/42; B01J 2229/40
USPC .......... 502/60, 439, 501, 514; 423/710, 711, 423/712
See application file for complete search history.

(56) References Cited

PUBLICATIONS

Cilla et al., "Geopolymer foams by gelcasting", Ceramics International (2014), 5723-5730.*
Tisler et al., "Acid and Thermal Treatment of Alkali-Activated Zeolite Foams", Minerals (2019), 9 719, 1-19.*
Murayama et al., "Zeolite synthesis from coal fly ash by hydrothermal reaction using various alkali sources", J. Chem Technol Biotechnol 77:280-286.*

* cited by examiner

*Primary Examiner* — Elizabeth D Wood
(74) *Attorney, Agent, or Firm* — DINSMORE & SHOHL LLP

(57) ABSTRACT

Disclosed are a zeolite-like material, and a preparation method and use thereof. In the disclosure, cyclic molecules of the zeolite-like material form a closed cage-like cavity structure with each other. The zeolite-like material is synthesized using an inorganic solid waste as a raw material.

8 Claims, 3 Drawing Sheets

ZEOLITE-LIKE MATERIAL, AND PREPARATION METHOD AND USE THEREOF

CROSS-REFERENCE TO RELATED APPLICATION

This patent application claims the benefit and priority of Chinese Patent Application No. 202210185397.0, entitled "Zeolite-like material, and preparation method and use thereof" filed on Feb. 28, 2022, the disclosure of which is incorporated by reference herein in its entirety as part of the present application.

FIELD OF THE INVENTION

The present disclosure relates to the technical field of adsorption materials, in particular to a zeolite-like material, and a preparation method and use thereof.

BACKGROUND OF THE INVENTION

Zeolite molecular sieves, as the most widely-used catalyst and adsorbent, have been used in industry in a large scale. However, industrially-prepared molecular sieves have high requirements on a purity of raw materials, and the production process thereof are complex and high in costs. Therefore, it has become a current research hotspot in development of zeolite substitute materials with an excellent performance and use thereof in catalysis and adsorption.

Zeolite-like material is a new type of inorganic and green cementitious material. Amorphous phases and three-dimensional aluminosilicate network structures are formed by polymerization of aluminosilicate materials dissolved in an alkali activator solution at room temperature or elevated temperature. The zeolite-like material has a structure similar to that of the zeolite molecular sieve (FIG. 7). The zeolite-like material (FIG. 8), due to a unique three-dimensional network structure, not only has excellent properties such as high pressure resistance, acid resistance and alkali resistance, but also could stabilize toxic and harmful impurities in solid wastes. Studies have shown that cyclic molecules in a geopolymer form a closed cage-like cavity structure with each other, to cure toxic metal ions and other harmful substances in the cavity. In addition, a "cage-type" network skeleton, which is hardly affected by nuclear radiation, could also cure radioactive nuclear substances.

However, at present, there is no research on the preparation of a porous zeolite-like material from hazardous solid wastes such as pure waste incineration fly ash.

SUMMARY OF THE INVENTION

An object of the present disclosure is to provide a zeolite-like material, and a preparation method and use thereof. The zeolite-like material is synthesized using an inorganic solid waste as a raw material, and has an excellent performance in catalysis.

To achieve the above object, the present disclosure provides the following technical solutions.

The present disclosure provides a method for preparing a zeolite-like material, including the following steps:

mixing an inorganic solid waste and an alkali activator, and conducting an alkali activating reaction to obtain an activated waste, where the alkali activator includes the following components in percentage by mass: 20% to 35% of potassium hydroxide, 15% to 20% of potassium silicate and 50% to 60% of water, and the inorganic solid waste has a total mass content of silica and alumina of greater than or equal to 10%;

mixing the activated waste with a binder to obtain a mixture, and precuring the mixture under heating to obtain a precured waste, where the binder is selected from the group consisting of an aluminum oxide and an aluminum salt;

mixing the precured waste with a foaming agent, and foaming to obtain a foamed waste; and forcibly curing the foamed waste to obtain a cured waste, and calcining the cured waste to obtain the zeolite-like material.

In some embodiments, the inorganic solid waste includes one or more selected from the group consisting of waste incineration fly ash, coal ash, sludge, coal gangue, and blast furnace slag.

In some embodiments, the alkali activator is used in an amount of 80% to 120% by mass of the inorganic solid waste.

In some embodiments, the binder is used in an amount of 10% to 20% by mass of the inorganic solid waste.

In some embodiments, the precuring is conducted at 80° C. for 5 min to 10 min.

In some embodiments, the foaming agent includes a hydrogen peroxide solution with a volume concentration of 3%; and the foaming agent is used in an amount of 150% to 300% by mass of the inorganic solid waste.

In some embodiments, during the foaming, a foam stabilizer is further added thereto in an amount of 20% to 50% by mass of the inorganic solid waste; and the foam stabilizer includes one or more selected from the group consisting of oleic acid, a protein, vegetable oil, Tween-80 (polyoxyethylene sorbitan monooleate), Triton X-100 (octylphenol ethoxylate), sodium dodecyl sulfate, and sodium dodecyl benzene sulfonate.

In some embodiments, the forcibly curing is conducted at 80° C. for 48 h to 72 h; and the calcining is conducted at 400° C. to 600° C. for not less than 3 h.

The present disclosure further provides a zeolite-like material prepared by the method as described in the above technical solutions.

The present disclosure further provides use of the zeolite-like material in catalysis.

The present disclosure provides a method for preparing a zeolite-like material, including the following steps: mixing an inorganic solid waste and an alkali activator, and conducting an alkali activating reaction to obtain an activated waste, where the alkali activator includes the following components in percentage by mass: 20% to 35% of potassium hydroxide, 15% to 20% of potassium silicate and 50% to 60% of water, and the inorganic solid waste has a total mass content of silica and alumina of greater than or equal to 10%; mixing the activated waste with a binder to obtain a mixture, and precuring the mixture under heating to obtain a precured waste, where the binder is selected from the group consisting of an aluminum oxide and an aluminum salt; mixing the precured waste with a foaming agent, and foaming to obtain a foamed waste; and forcibly curing the foamed waste to obtain a cured waste, and calcining the cured waste to obtain the zeolite-like material.

Inorganic solid waste is rich in silicon and aluminum components. In the present disclosure, the alkali activating reaction is conducted under an action of a strong alkali to promote dissolution of the silicon and aluminum in the inorganic solid waste, to form a silicon-oxygen tetrahedron and an aluminum-oxygen tetrahedron. The alkali activator includes potassium hydroxide and potassium silicate. The potassium silicate could be used as an external silicon source. Since a Si—O—Si bond has a strength higher than that of Si—O—Al and Al—O—Al bonds, it may be concluded that the higher Si content is beneficial to the formation of high-strength Si—O—Si bonds to improve structure stability of the zeolite-like material, while the low volume of potassium ions is beneficial to promoting the complete performing of subsequent polycondensation reaction. After the alkali activating reaction, the precuring is conducted. During the precuring, polycondensation between the silicon-oxygen tetrahedron and the aluminum-oxygen tetrahedron is initially conducted to form a silica-alumina gel (oligomer), which could prevent the foaming agent from destroying the structure stability of the material, and the gel is conducive to the formation of uniform and fine pore structures. Then the foaming agent is added to improve a porosity of the material; forcibly curing is conducted, through which the oligomer is further condensed to form a three-dimensional network structure; and the zeolite-like material is obtained after calcining and burning off the organic matters.

In the present disclosure, cyclic molecules of the zeolite-like material form a closed cage-like cavity structure with each other, such that toxic metal ions and other harmful substances could be cured in the cavity, which avoids an influence of impurities contained in solid wastes on material synthesis and product structure performances, and solves a problem that zeolite molecular sieves have strict requirements on raw materials.

In the present disclosure, the preparation method has a simple process and low cost; the raw material is the inorganic solid waste rich in silicon and aluminum components, with dual benefits of economy and environmental protection.

In the present disclosure, the prepared product has a zeolite-like structure, and has characteristics such as excellent durability, high-temperature resistance, acid resistance, high alkali-corrosion resistance, being able to cure heavy metal ions and radioactive elements, and a flexible and adjustable structure, and thereby could be used in many fields such as catalysis, adsorption, and ion exchange.

DETAILED DESCRIPTION OF THE EMBODIMENTS

Figure 1:
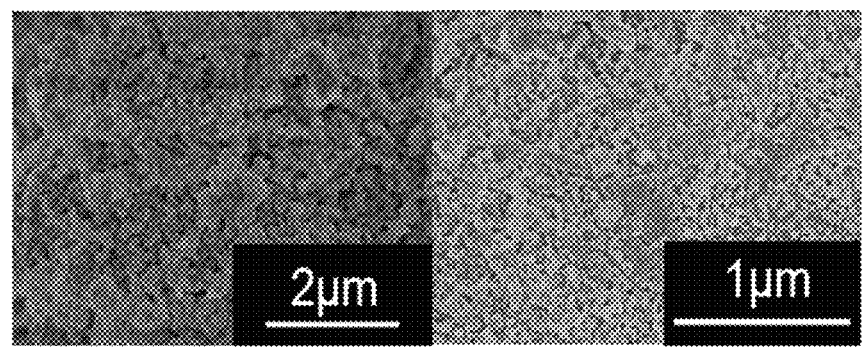
FIG. 1 shows a scanning electron microscope (SEM) image of the contaminated soil-derived zeolite-like material as prepared in Example 1.

The present disclosure provides a method for preparing a zeolite-like material, including the following steps:

mixing an inorganic solid waste and an alkali activator, and conducting an alkali activating reaction to obtain an activated waste, where the alkali activator includes the following components in percentage by mass: 20% to 35% of potassium hydroxide, 15% to 20% of potassium silicate and 50% to 60% of water, and the inorganic solid waste have a total mass content of silica and alumina of greater than or equal to 10%;

mixing the activated waste with a binder to obtain a mixture, and precuring the mixture under heating to obtain a precured waste, where the binder is selected from the group consisting of an aluminum oxide and an aluminum salt;

mixing the precured waste with a foaming agent, and foaming to obtain a foamed waste; and forcibly curing the foamed waste to obtain a cured waste, and calcining the cured waste to obtain the zeolite-like material.

In the present disclosure, the inorganic solid waste and the alkali activator are mixed for alkali activating reaction to obtain the activated waste.

In some embodiments, the inorganic solid waste have a total mass content of silica and the alumina of greater than or equal to 10%. The silica and the alumina in the inorganic solid waste are used as reaction raw materials. In some embodiments, the inorganic solid waste includes one or more selected from the group consisting of waste incineration fly ash, coal ash, sludge, coal gangue, and blast furnace slag; under the condition that the inorganic solid waste includes multiple components of the above wastes, there is no special requirement for a ratio of each waste, as long as the inorganic solid waste have a total mass content of silica and alumina of greater than or equal to 10%. In some embodiments, under the condition that the solid waste contains organic matters, a high temperature treatment is conducted on the solid waste to remove the organic matters. In some embodiments, the inorganic solid waste has a particle size of less than 200 mesh.

In the present disclosure, the alkali activator includes the following components in percentage by mass: 20% to 35% of potassium hydroxide, 15% to 20% of potassium silicate, and 50% to 60% of water.

In some embodiments, the alkali activator is used in an amount of 80% to 120%, preferably 90% to 110%, and more preferably 95% to 105% by mass of the inorganic solid waste.

In some embodiments, the alkali activating reaction is conducted at room temperature. In some embodiments, the alkali activating reaction is conducted for 20 min to 30 min. In some embodiments, the alkali activating reaction is conducted under stirring.

In the present disclosure, the alkali activating reaction is conducted under an action of a strong alkali to promote dissolution of the silicon and aluminum in the inorganic solid waste, to form a silicon-oxygen tetrahedron and an aluminum-oxygen tetrahedron. The alkali activator includes potassium hydroxide and potassium silicate. The potassium silicate could be used as an external silicon source. Since a Si—O—Si bond has a strength higher than that of Si—O—Al and Al—O—Al bonds, it may be concluded that the higher Si content is beneficial to the formation of high-strength Si—O—Si bonds to improve structure stability of the zeolite-like material, while the low volume of potassium ions is beneficial to promoting the complete performing of subsequent polycondensation reaction.

In the present disclosure, the activated waste is mixed with a binder, and then precured under heating to obtain a precured waste.

In the present disclosure, the binder is an aluminum oxide or an aluminum salt. In some embodiments, the aluminum oxide is hydrated alumina. In some embodiments, the aluminium salt includes one selected from the group consisting of polyaluminium chloride and aluminium sulfate. Aluminum-containing chemicals as a binder have an agglomeration effect, and could promote hardening of dispersed oxide suspensions due to agglomeration, thereby improving an efficiency of the polycondensation reaction and enhancing a durability of the product. Meanwhile, the aluminum-containing chemicals as a binder could also adjust a silicon-to-aluminum ratio of a precursor slurry, since in addition to silicon, the polycondensation reaction also requires a certain amount of aluminum.

In some embodiments, the binder is used in an amount of 10% to 20%, preferably 12% to 18%, and more preferably 14% to 16% by mass of the inorganic solid waste.

In some embodiments, the activated waste is mixed with the binder by a process comprising adding the binder to the activated waste.

In some embodiments, the precuring is conducted at 80° C. In some embodiments, the precuring is conducted for 5 min to 10 min. During the precuring, polycondensation is initially conducted between the silicon-oxygen tetrahedron and the aluminum-oxygen tetrahedron to form a silicon-alumina gel (as an oligomer). The silica-alumina gel could prevent the foaming agent from destroying the structural stability of the material, and the gel is conducive to the formation of uniform and fine pore structures. This is because more gelling materials lead to thicker pore walls around the bubbles after the introduction of bubbles; thereby, the bubbles are not easily broken during the stirring, and small bubbles are not easily merged into large bubbles.

In the present disclosure, the precured waste is mixed with a foaming agent, and then foamed to obtain a foamed waste.

In some embodiments, the foaming agent includes a hydrogen peroxide solution. In some embodiments, the hydrogen peroxide solution has a volume concentration of 3%. In some embodiments, the foaming agent is used in an amount of 150% to 300%, preferably 180% to 280%, and more preferably 200% to 250% by mass of the inorganic solid waste.

In some embodiments, a foam stabilizer is further added during the foaming. In some embodiments, the foam stabilizer is used in an amount of 20% to 50%, preferably 25% to 45%, and more preferably 30% to 40% by mass of the inorganic solid waste. In some embodiments, the foam stabilizer includes one or more selected from the group consisting of oleic acid, a protein, vegetable oil, Tween-80, Triton X-100, sodium dodecyl sulfate, and sodium dodecyl benzene sulfonate. In some embodiments, the foam stabilizer includes oleic acid. In some embodiments, the oleic acid has a mass concentration of not less than 99%. In the present disclosure, the foam stabilizer enables the foam to be uniform and fine.

In some embodiments, the precured waste is mixed with the foaming agent by adding the foaming agent dropwise to the precured waste under stirring; under the condition that a foam stabilizer is also included, the foaming is conducted by adding the foaming agent and the foam stabilizer dropwise to the precured waste under stirring.

In the present disclosure, the uniform and fine pore structures are formed during the foaming, and a porosity of the zeolite-like material is improved.

In the present disclosure, the foamed waste is forcibly cured, and then calcined to obtain the zeolite-like material.

In some embodiments, the forcibly curing is conducted at 80° C. In some embodiments, the forcibly curing is conducted for 48 h to 72 h, preferably 52 h to 68 h, and more preferably 55 h to 60 h. In some embodiments, the foamed waste is forcibly cured in a mold. During the forcibly curing, the oligomer is further condensed to form a three-dimensional network structure.

In some embodiments, the cured waste is thoroughly ground and then calcined.

In some embodiments, the calcining is conducted at 400° C. to 600° C., preferably 450° C. to 550° C. In some embodiments, the calcining is conducted for not less than 3 h, preferably 3 h. In some embodiments, the calcining is conducted in an air atmosphere. In the present disclosure, organic matters such as the foam stabilizer are burn out by calcining.

In the present disclosure, cyclic molecules of the zeolite-like material form a closed cage-like cavity structure with each other, such that toxic metal ions and other harmful substances could be cured in the cavity, which avoids an influence of impurities contained in solid wastes on material synthesis and product structure performances, and solves a problem that zeolite molecular sieves have strict requirements on raw materials.

The present disclosure further provides a zeolite-like material prepared by the method as described in the above technical solutions. In some embodiments, the zeolite-like material has a specific surface area of 5 m2/g to 10 m2/g. In some embodiments, the zeolite-like material has a pore size of 9 nm to 12 nm. In some embodiments, the zeolite-like material has a pore volume of 0.02 cm3/g to 0.06 cm3/g.

In the present disclosure, from the perspective of spatial structure, the zeolite-like material is an aluminosilicate polymer with a three-dimensional network structure formed by [SiO4] tetrahedron and [AlO4] tetrahedron alternately ligated by shared vertex oxygen atoms; the negative charge generated by Al tetracoordination is balanced by cations (such as Na+, K+, Li+, Ca2+, Ba2+, NH4+ and H3O+) present in the zeolite-like material structure. The zeolite-like material is in an amorphous state, and a center of an XRD peak of the amorphous material is located at a position where 2θ is from 27° to 30°.

The present disclosure further provides use of the zeolite-like material in catalysis.

In some embodiments, the zeolite-like material is used as a catalyst carrier. There are no special requirements on the specific preparation method and use conditions of the catalyst, and any preparation method and use conditions well-known in the art may be used.

In some embodiments, the catalyst is prepared by an ultra-wet impregnation method.

In some embodiments, the ultra-wet impregnation method includes the following steps:

mixing the zeolite-like material with an active metal salt solution to obtain a mixture, filtering the mixture to obtain a solid, and subjecting the solid to a drying, a calcination and a reduction in sequence to obtain the catalyst.

In the present disclosure, there is no special requirement on an amount of the active metal salt solution, and the amount may be selected according to the composition of a target catalyst. In the present disclosure, there is no special requirement on conditions for calcination and reduction, and appropriate conditions may be selected according to the type of active metal.

In some embodiments, under the condition that the active metal is Ni, the calcination is conducted at 550° C. for 4 h in flowing air; and in some embodiments, the reduction is conducted at 500° C. for 1 h in a H2/N2 mixed atmosphere. In some embodiments, the H2/N2 mixed atmosphere has a volume content of H2 of 75%.

The following describes in detail the zeolite-like material, and the preparation method and use thereof provided by the present disclosure with reference to the examples which, however, are not to be construed as limiting the protection scope of the present disclosure.

Example 1

Preparation of a Zeolite-Like Material from a Pesticide-Contaminated Soil after High-Temperature Treatment A pesticide-contaminated soil was subjected to a high-temperature treatment at 800° C. to remove organic matters. 5 g of the resulting pesticide-contaminated soil after high-temperature treatment was taken and used as an inorganic solid waste, an alkali activator in an amount of 80% by mass of the inorganic solid waste was added, and they were subjected to alkali activating reaction under stirring at room temperature for 20 min, where the alkali activator consisted of 35 wt % of KOH, 15 wt % of K2SiO3 and 50 wt % of water. Then Al2O3 in an amount of 10% by mass of the inorganic solid waste was added as a binder, and the resulting mixture was stirred to be uniform to obtain a slurry. The obtained slurry was precured for 5 min in an incubator at 80° C. Then an oleic acid solution (with a mass concentration of not less than 99%) in an amount of 20% by mass of the inorganic solid waste and a H2O2 solution (with a concentration of 3% by volume) in an amount of 150% by mass of the inorganic solid waste were added dropwise under stirring to generate a foam, and the foam was placed in a mold and polymerized in an incubator at 80° C. for 72 h. Finally, the foam was demolded, fully ground, and calcined in a furnace at 400° C. for 3 h to obtain a contaminated soil-derived zeolite-like material.

Structural properties of the contaminated soil-derived zeolite-like material were analyzed using nitrogen adsorption method. The results show that the contaminated soil-derived zeolite-like material has a specific surface area of 5.53 m2/g, an average pore size of 9.64 nm, and a pore volume of 0.024 cm3/g.

Figure 2:
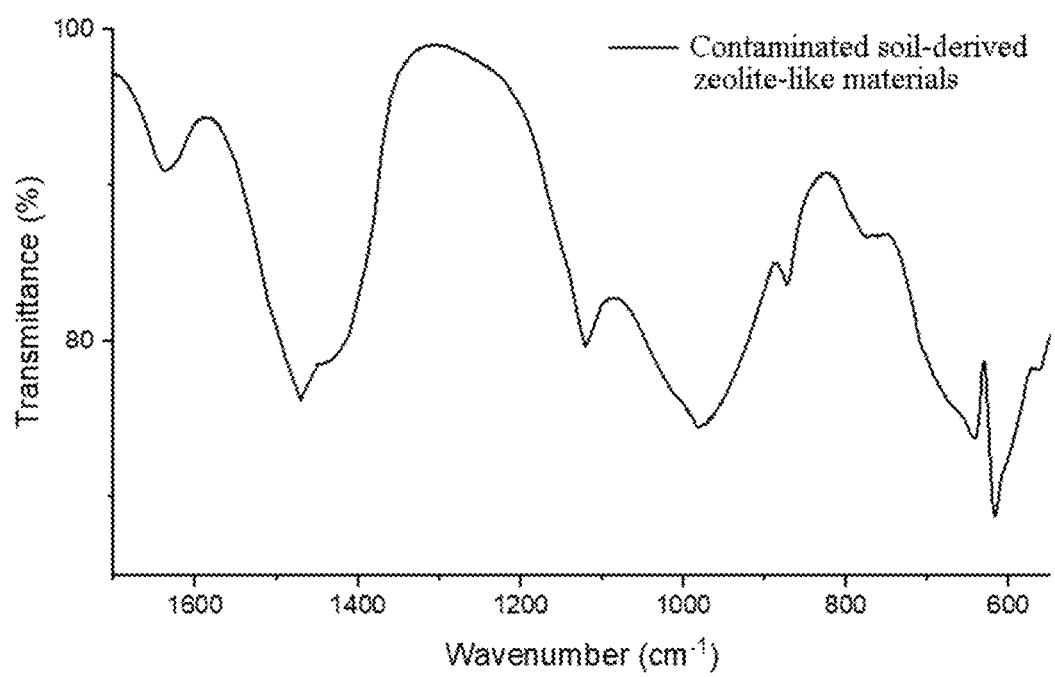
FIG. 2 shows a fourier transform infrared spectroscopy (FTIR) characterization of the contaminated soil-derived zeolite-like material as prepared in Example 1.

FIG. 1 shows a SEM image of the contaminated soil-derived zeolite-like material as prepared in Example 1. FIG. 1 shows that the contaminated soil-derived zeolite-like material has a surface structure formed by agglomeration of fine particles, and because the structure is relatively scattered, the formation of an internal cage-like pore structure can be seen. This proves the existence of gel, which is a main product of polycondensation, and the formation of a three-dimensional silica-alumina framework. A chemical bond structure of the contaminated soil-derived zeolite-like material was analyzed using FTIR, and the results are shown in FIG. 2. It is found that a peak at 1009 cm−1, which is attributed to stretching vibration of Si—O—Si, is generated. This peak represents a successful generation of the three-dimensional silica-alumina framework of the zeolite-like material. T—O—T (T is silicon or aluminum) is a chemical bonding form of a zeolite-like material framework, and the predominant type of chemical bonds in the silica-alumina framework of the zeolite-like material determines the strength and durability of the material. In addition, an absorption band from 1423 cm−1 to 1466 cm−1 may also be related to asymmetric stretching vibration of Si—O or Al—O bonds. Combining FTIR and SEM analysis, it could be concluded that the silica-alumina framework and gel structure of the material have been successfully formed, which may render excellent properties of the zeolite-like material, which needs to be further verified by synthesizing a catalyst and conducting reactions.

Use Example 1

Catalyst Preparation:

A non-precious metal-based hydrogenation catalyst was prepared by an ultra-wet impregnation method. The zeolite-like material of Example 1 was added to a Ni(NO3)2·6H2O aqueous solution, stirred at room temperature for 12 h, filtered and washed with pure water for 3 times, and dried at 80° C. for 10 h. The resulting powder was calcined at 550° C. for 4 h in flowing air, and then reduced for 1 h at 500° C. in a H2/N2 gas mixture with a H2 volume content of 75%, to obtain a catalyst with a metal Ni loading amount of 4 wt %.

Catalytic Reaction:

Catalytic hydrogenation of the levulinic acid to prepare γ-valerolactone was conducted using 0.5 g of the catalyst, 1 mL of levulinic acid and 10 mL of isopropanol under an initial hydrogen pressure of 4 MPa and at 200° C. for 4 h. The results show that the catalyst has a good performance, a conversion rate of levulinic acid reaches 100%, and a yield of γ-valerolactone reaches 95%; after five cycles of the experiment, the conversion rate of levulinic acid still reaches 100%, and the yield of γ-valerolactone does not decrease significantly, which is 85%.

Example 2

Preparation of a Zeolite-Like Material from Waste Incineration Fly Ash 5 g of waste incineration fly ash was taken and used as an inorganic solid waste, and an alkali activator in an amount of 110% by mass of the inorganic solid waste was added, and they were subjected to alkali activating reaction under stirring at room temperature for 25 min, where the alkali activator consisted of 20 wt % of KOH, 20 wt % of K2SiO3 and 60 wt % of water. Then Al2O3 in an amount of 20% by mass of the inorganic solid waste was added as a binder, and the resulting mixture was stirred to be uniform to obtain a slurry. The obtained slurry was precured for 8 min in an incubator at 80° C. Then an oleic acid solution (with a mass concentration of not less than 99%) in an amount of 40% by mass of the inorganic solid waste and a H2O2 solution (with a concentration of 3% by volume) in an amount of 250% by mass of the inorganic solid waste were added dropwise under stirring to generate a foam, and the foam was placed in a mold and polymerized in an incubator at 80° C. for 50 h. Finally, the foam was demolded, fully ground, and calcined in a furnace at 500° C. for 3 h to obtain a waste incineration fly ash-derived zeolite-like material.

Structural properties of the waste incineration fly ash-derived zeolite-like material were analyzed using nitrogen adsorption method. The results show that the waste incineration fly ash-derived zeolite-like material has a specific surface area of 9.38 m2/g, a pore size of 11.89 nm, and a pore volume of 0.06 cm3/g.

Figure 3:
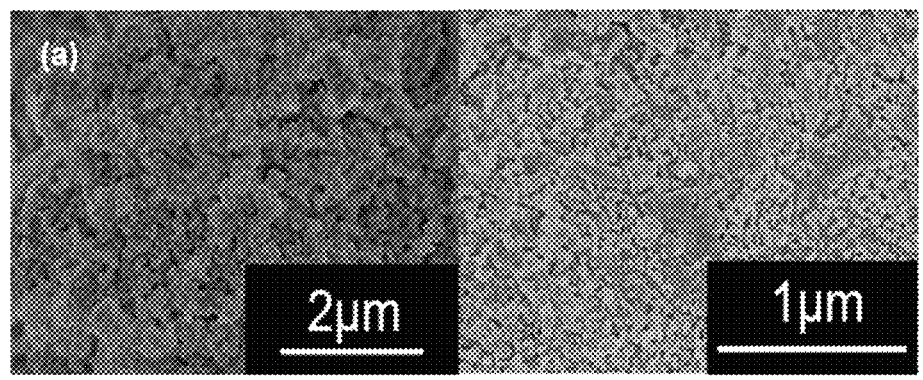
FIG. 3 shows a SEM image of the waste incineration fly ash-derived zeolite-like material as prepared in Example 2.
Figure 4:
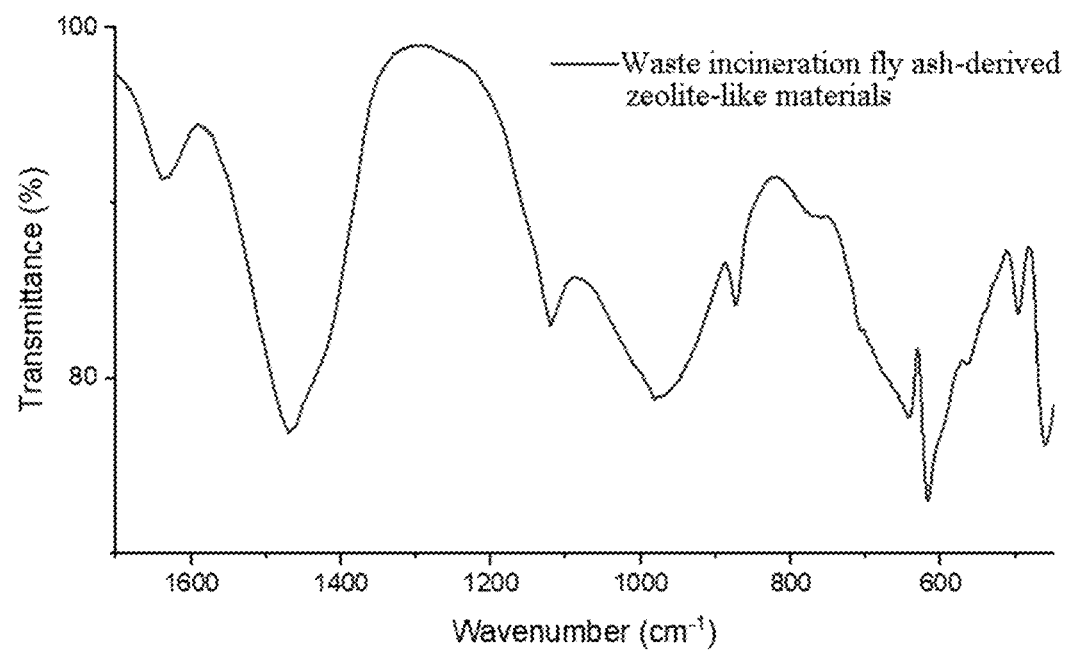
FIG. 4 shows a FTIR characterization of the waste incineration fly ash-derived zeolite-like material as prepared in Example 2.

FIG. 3 shows a SEM image of the waste incineration fly ash-derived zeolite-like material as prepared in Example 2. FIG. 3 shows that the waste incineration fly ash-derived zeolite-like material has a surface structure formed by agglomeration of fine particles, possibly due to the presence of gel, which is a main product of the polycondensation. A chemical bond structure of the waste incineration fly ash-derived zeolite-like material was analyzed using FTIR, and the results are shown in FIG. 4. It is found that a peak at 980 cm−1 to 1113 cm−1 is generated which is attributed to stretching vibration of Si—O—Si. This peak represents a successful generation of the three-dimensional silica-alumina framework of the zeolite-like material. T—O—T (T is silicon or aluminum) is a chemical bonding form of a zeolite-like material framework, and the predominant type of chemical bonds in the silica-alumina framework of the zeolite-like material determines the strength and durability of the material. In addition, an absorption band at 1461 cm−1 may also be related to asymmetric stretching vibration of Si—O or Al—O bonds. Combining FTIR and SEM analysis, it could be concluded that the silica-alumina framework and gel structure of the material have been successfully formed, which may render excellent properties of the zeolite-like material, which needs to be further verified by synthesizing a catalyst and conducting reactions.

Use Example 2

The catalyst preparation and catalytic reaction conditions were the same as in Use Example 1, except that the contaminated soil-derived zeolite-like material of Example 1 was replaced with the waste incineration fly ash-derived zeolite-like material of Example 2.

The results show that the catalyst has a good performance, a conversion rate of levulinic acid reaches 100%, and a yield of γ-valerolactone reaches 98%; after five cycles of the experiment, the conversion rate of levulinic acid still reaches 100%, and the yield of γ-valerolactone does not decrease significantly, which is 96%.

Example 3

Preparation of a Zeolite-Like Material from Sludge 5 g of sludge (pretreated by: drying, pulverizing, sieving by a 200-mesh sieve) was taken and used as an inorganic solid waste, and an alkali activator in an amount of 120% by mass of the inorganic solid waste was added, and they were subjected to alkali activating reaction under stirring at room temperature for 30 min, where the alkali activator consisted of 25 wt % of KOH, 20 wt % of K2SiO3 and 55 wt % of water. Then Al2O3 in an amount of 15% by mass of the inorganic solid waste was added as a binder, and the resulting mixture was stirred to be uniform to obtain a slurry. The obtained slurry was precured for 10 min in an incubator at 80° C. Then an oleic acid solution (with a mass concentration of not less than 99%) in an amount of 50% by mass of the inorganic solid waste and a H2O2 solution (with a concentration of 3% by volume) in an amount of 300% by mass of the inorganic solid waste were added dropwise under stirring to generate a foam, and the foam was placed in a mold and polymerized in an incubator at 80° C. for 48 h. Finally, the foam was demolded, fully ground, and calcined in a furnace at 600° C. for 3 h to obtain a sludge-derived zeolite-like material.

Structural properties of the sludge-derived zeolite-like material were analyzed using nitrogen adsorption method. The results show that the sludge-derived zeolite-like material has a specific surface area of 9.30 m2/g, a pore size of 11.64 nm, and a pore volume of 0.05 cm3/g.

Figure 5:
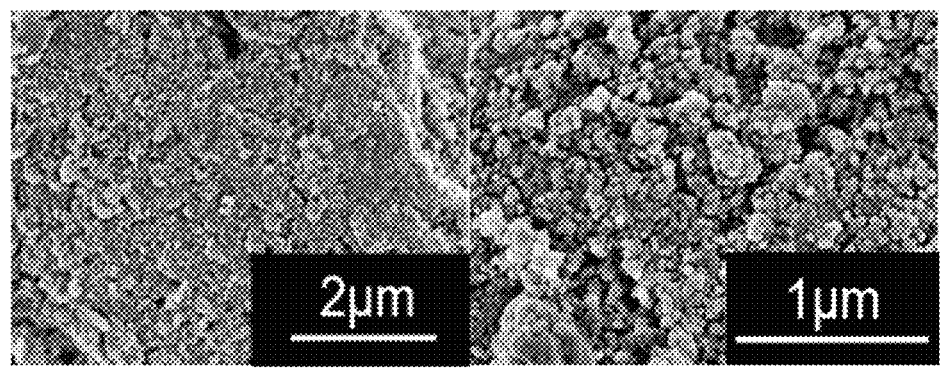
FIG. 5 shows a SEM image of the sludge-derived zeolite-like material as prepared in Example 3.
Figure 6:
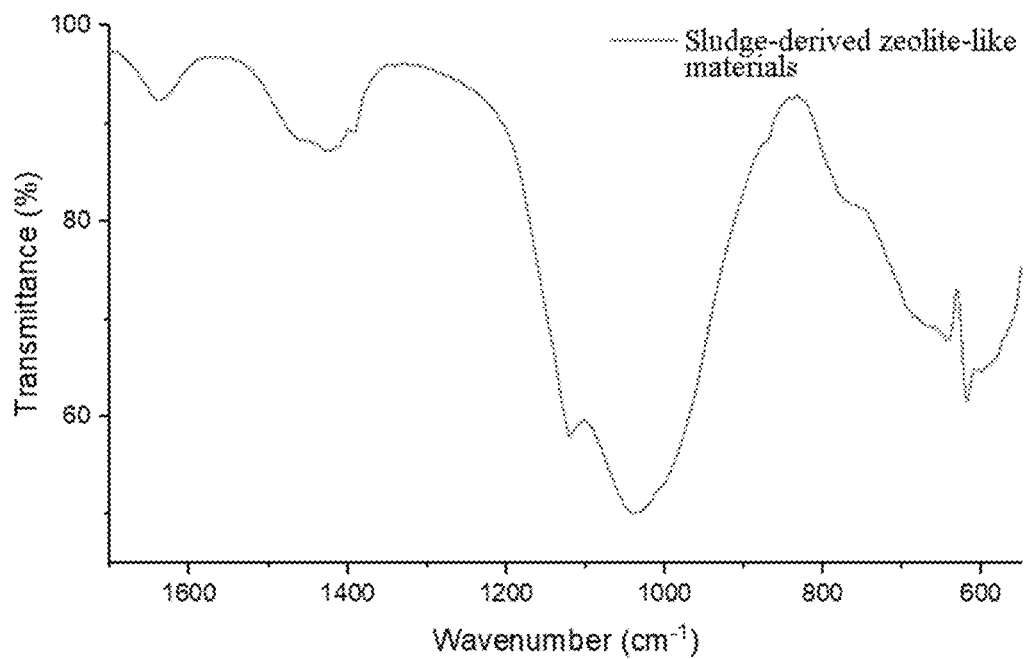
FIG. 6 shows a FTIR characterization of the sludge-derived zeolite-like material as prepared in Example 3.
Figure 7:
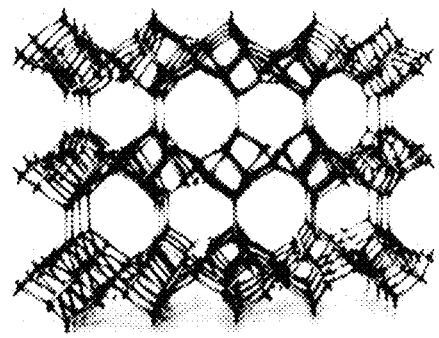
FIG. 7 shows a structural model of a zeolite material.
Figure 8:
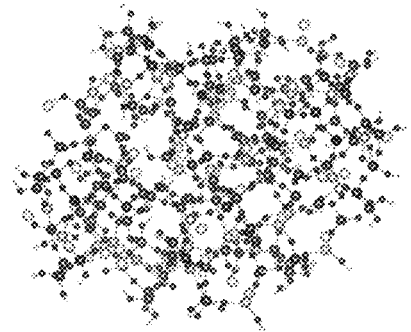
FIG. 8 shows a structural model of the zeolite-like material.

FIG. 5 shows a SEM image of the sludge-derived zeolite-like material as prepared in Example 3. The structural properties of the material were analyzed using nitrogen adsorption method, and it is found that the sludge-derived zeolite-like material has a relatively high specific surface area and a mesoporous structure. The SEM image shows that the sludge-derived zeolite-like material has a surface structure formed by agglomeration of fine particles, possibly due to the presence of gel, which is a main product of the polycondensation. A chemical bond structure of the sludge-derived zeolite-like material was analyzed using FTIR, and the results are shown in FIG. 6. It is found that a peak at 1113 cm−1 is generated which is attributed to stretching vibration of Si—O—Si. This peak represents a successful generation of the three-dimensional silica-alumina framework of the zeolite-like material. T—O—T (T is silicon or aluminum) is a chemical bonding form of a zeolite-like material framework, and the predominant type of chemical bonds in the silica-alumina framework of the zeolite-like material determines the strength and durability of the material. In addition, an absorption band at 1418 cm−1 may also be related to asymmetric stretching vibration of Si—O or Al—O bonds. Combining FTIR and SEM analysis, it could be concluded that the silica-alumina framework and gel structure of the material have been successfully formed, which may render excellent properties of the zeolite-like material, which needs to be further verified by synthesizing a catalyst and conducting reactions.

Use Example 3

The catalyst preparation and catalytic reaction conditions were the same as in Use Example 1, except that the contaminated soil-derived zeolite-like material of Example 1 was replaced with the sludge-derived zeolite-like material of Example 3.

The results show that the catalyst has a good performance, a conversion rate of levulinic acid reaches 100%, and a yield of γ-valerolactone reaches 96%; after five cycles of the experiment, the conversion rate of levulinic acid still reaches 100%, and the yield of γ-valerolactone does not decrease significantly, which is 92%.

Comparative Example 1

A 5 wt % Ni/HZSM-5-50 catalyst was prepared by a wet impregnation method as follows:

A commercial HZSM-5 zeolite was added to a Ni(NO3)2·6H2O aqueous solution, and evaporated in a vacuum thermostatic rotary evaporator at 60° C. The obtained dried powder was calcined at 600° C. for 5 h, and then reduced in H2 at 500° C. for 4 h, to obtain the 5 wt % Ni/HZSM-5-50 catalyst.

Catalytic conversion of levulinic acid to γ-valerolactone was conducted using 2 g of levulinic acid, 1 g of the catalyst, and 20 mL of water, at 210° C. and an initial hydrogen pressure of 3 MPa for 2 h, obtaining γ-valerolactone (GVL) with a yield reaching 100%. (Reference: Zhang D, Zhao Y P, Fan X, et al., Catalytic Hydrogenation of Levulinic Acid into Gamma-Valerolactone Over Ni/HZSM-5 Catalysts [J]. Catalysis Surveys from Asia. 2018, Vol. 22 (No. 3): 129-135.)

Comparative Example 2

A zeolite was synthesized using waste incineration fly ash as a raw material by a traditional alkali melting method as follows:

10 g of the waste incineration fly ash was mixed with 10 g of anhydrous sodium carbonate to be uniform, and the resulting mixture was placed in a muffle furnace and calcined at 850° C. for 2 h, and then cooled. The cooled material was mixed with NaOH having a concentration of 2 mol/L in a liquid-to-solid ratio of 10:1, and the resulting mixture was subjected to a hydrothermal reaction at 90° C. for 14 h and then dried to obtain the zeolite.

The catalyst preparation and catalytic reaction conditions were the same as in Use Example 1, except that the zeolite-like material of Example 1 was replaced with the zeolite of Comparative Example 2. The results show that the catalyst has a poor performance, leading to a yield of γ-valerolactone close to 0%.

It can be seen from the results of Examples and Comparative Example 1 that the catalyst with a zeolite-like prepared from inorganic solid waste as a catalyst carrier has a good catalytic performance, achieving a technical effect equivalent to of the catalyst with zeolite as a carrier (Comparative Example 1). It can be seen from the results of Comparative Example 2 that, when the zeolite is prepared by using the inorganic solid waste, the formation of a zeolite structure will be inhibited due to an insufficient silicon-alumina ratio of the raw material or excessive impurity ions, resulting in a poor catalytic performance of the obtained catalyst.

The above descriptions are merely preferred embodiments of the present disclosure. It should be noted that those of ordinary skill in the art may further make several improvements and modifications without departing from the principle of the present disclosure, and such improvements and modifications shall be deemed as falling within the protection scope of the present disclosure.

What is claimed is:

1. A method for preparing a zeolite-like material having amorphous phases and three-dimensional aluminosilicate network structures, comprising the following steps:

mixing an inorganic solid waste and an alkali activator, and conducting an alkali activating reaction to obtain an activated waste, wherein the alkali activator comprises the following components in percentage by mass: 20% to 35% of potassium hydroxide, 15% to 20% of potassium silicate, and 50% to 60% of water, and the inorganic solid waste have a total mass content of silica and alumina of greater than or equal to 10%;

mixing the activated waste with a binder to obtain a mixture, and precuring the mixture under heating to obtain a precured waste, wherein the binder is selected from the group consisting of an aluminum oxide and an aluminum salt;

mixing the precured waste with a foaming agent, and foaming to obtain a foamed waste; and forcibly curing the foamed waste to obtain a cured waste, and calcining the cured waste to obtain the zeolite-like material, having amorphous phases and three-dimensional aluminosilicate network structures.

2. The method of claim 1, wherein the inorganic solid waste comprises one or more selected from the group consisting of waste incineration fly ash, coal ash, sludge, coal gangue, and blast furnace slag.

3. The method of claim 1, wherein the alkali activator is used in an amount of 80% to 120% by mass of the inorganic solid waste.

4. The method of claim 1, wherein the binder is used in an amount of 10% to 20% by mass of the inorganic solid waste.

5. The method of claim 1, wherein the precuring is conducted at 80° C. for 5 min to 10 min.

6. The method of claim 1, wherein the foaming agent comprises a hydrogen peroxide solution with a volume concentration of 3%; and the foaming agent is used in an amount of 150% to 300% by mass of the inorganic solid waste.

7. The method of claim 6, wherein during the foaming, a foam stabilizer is further added in an amount of 20% to 50% by mass of the inorganic solid waste; and the foam stabilizer comprises one or more selected from the group consisting of oleic acid, a protein, vegetable oil, polyoxyethylene sorbitan monooleate, octylphenol ethoxylate, sodium dodecyl sulfate, and sodium dodecyl benzene sulfonate.

8. The method of claim 1, wherein the forcibly curing is conducted at 80° C. for 48 h to 72 h; and the calcining is conducted at 400° C. to 600° C. for not less than 3 h.

* * * * *